(12) United States Patent
Khodak et al.

(10) Patent No.: US 8,160,718 B2
(45) Date of Patent: Apr. 17, 2012

(54) METHOD AND APPARATUS FOR PERFORMING WARMING THERAPY UTILIZING MATRIX HEATING

(75) Inventors: Andrei Khodak, Hatfield, PA (US); Peter D. Sabota, Warminster, PA (US)

(73) Assignee: Draeger Medical Systems, Inc., Telford, PA (US)

( * ) Notice: Subject to any disclaimer, the term of this patent is extended or adjusted under 35 U.S.C. 154(b) by 1140 days.

(21) Appl. No.: 12/006,658

(22) Filed: Jan. 4, 2008

(65) Prior Publication Data
US 2009/0177257 A1    Jul. 9, 2009

(51) Int. Cl.
*A61G 11/00* (2006.01)
(52) U.S. Cl. .............. 607/100; 607/96; 600/22
(58) Field of Classification Search .......... 607/96; 5/421; 600/22
See application file for complete search history.

(56) References Cited

U.S. PATENT DOCUMENTS

| | | | | |
|---|---|---|---|---|
| 4,969,459 A * | 11/1990 | Gusakov | ................. | 607/100 |
| 5,138,138 A | 8/1992 | Theilacker et al. | ........... | 219/528 |
| 5,285,054 A | 2/1994 | Barsky | ................. | 219/543 |
| 5,817,003 A * | 10/1998 | Moll et al. | ................. | 600/22 |
| 5,948,303 A * | 9/1999 | Larson | ................. | 219/486 |
| 6,011,477 A | 1/2000 | Teodorescu et al. | ..... | 340/573.01 |
| 6,359,597 B2 | 3/2002 | Has-Yousef | ................. | 343/850 |
| 6,679,830 B2 * | 1/2004 | Kolarovic et al. | ................. | 600/22 |
| 6,718,128 B2 * | 4/2004 | Meyer et al. | ................. | 392/418 |
| 6,719,780 B1 | 4/2004 | Salmon et al. | ................. | 607/108 |
| 7,008,371 B2 * | 3/2006 | Goldberg et al. | ................. | 600/22 |
| 2001/0020303 A1 | 9/2001 | Endo et al. | ................. | 5/421 |
| 2005/0101872 A1 | 5/2005 | Sattler et al. | ................. | 600/483 |
| 2005/0271117 A1 | 12/2005 | Grassl et al. | ................. | 374/121 |
| 2005/0276309 A1 | 12/2005 | Koch | ................. | 374/208 |
| 2006/0041196 A1 | 2/2006 | Matthews et al. | ................. | 600/393 |
| 2006/0089546 A1 | 4/2006 | Mahony et al. | ................. | 600/310 |

FOREIGN PATENT DOCUMENTS

| | | |
|---|---|---|
| EP | 0 872 227 | 10/1998 |
| EP | 1795121 A2 | 6/2007 |
| WO | 02/062282 | 8/2002 |
| WO | 03/022189 | 3/2003 |
| WO | 2006/135865 | 12/2006 |

* cited by examiner

*Primary Examiner* — Linda Dvorak
*Assistant Examiner* — Jared W Pike
(74) *Attorney, Agent, or Firm* — DLA Piper LLP (US)

(57) ABSTRACT

An apparatus and method for performing warming therapy is described. In one exemplary embodiment, the apparatus includes a warming platform, a heating source, a controller, and a plurality sensors. The heating source comprises a plurality of heating elements forming a matrix, wherein each heating element is operable to heat a corresponding region of the warming platform. The controller is operatively coupled to the heating source for controlling the temperature in each region of the warming platform. The plurality of sensors are operatively coupled to the controller for sensing a physiological parameter of a patient (e.g., body temperature) residing on the warming platform, and providing one or more control signals to the controller for selectively controlling the heating elements.

20 Claims, 4 Drawing Sheets

METHOD AND APPARATUS FOR PERFORMING WARMING THERAPY UTILIZING MATRIX HEATING

FIELD OF THE INVENTION

This present invention relates generally to a method and apparatus for performing warming therapy on medical patients. More particularly, the present invention relates to a method and apparatus for performing warming therapy on medical patient utilizing matrix heating.

BACKGROUND OF THE INVENTION

Conventional devices performing warming therapy apply heat to the entire body of a patient situated on a mattress. Such devices are often used, for example, to warm infants immediately after they are born.

Figure 1:
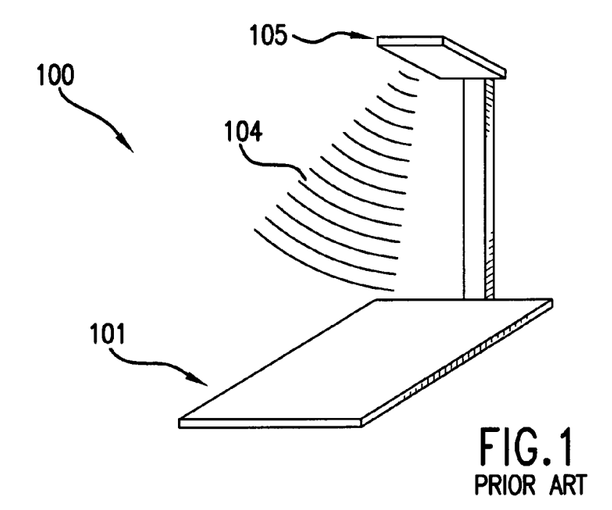
FIG. 1 is a perspective view of a conventional warming device.

One such conventional warming therapy device is shown in FIG. 1 of the present application. In particular, FIG. 1 shows a warming device 100, which includes a patient surface or mattress 101, and a radiant heat source 105. The radiant heat source 105 provides energy, in the form of infrared (IR) radiation 104, onto the entire mattress 101, and any patient which is situated thereon. However, most patients do not occupy the entirety of the mattress 101, and indeed, most patients (particularly infant patients), only occupy a small portion of the mattress 101. As a result, most of the radiation 104 emitted from the heating source 105 is wasted, resulting in energy and power inefficiencies, and increased heating of the area surrounding the warming device 100, and the room in which it is situated. Particularly, the unnecessary heating caused by the warming device 100 imposes an additional load on the climate control system. In other words, the excess warming requires the temperature control system (e.g., HVAC system controlled by a thermostat) in the surrounding room to work harder to maintain a constant and even temperature for the other occupants. Excess heating also affects the healthcare workers who are in close proximity to the warming device, leading to less comfortable working conditions. Wasted radiated energy also leads to excessive electric energy use by the warming device 100, which increases electric power consumption by the health care provider (e.g., hospital), and shortens the time the device can operate on battery power, such as during transport or power failure.

Additional drawbacks of conventional warming devices (such as shown in FIG. 1), include the use of contact-type sensors. Contact sensors, such as thermometers, often include lead wires which are coupled to the patient at one end (i.e., by medical tape or other adhesives), and to a controller unit of the warming device at the other end. As will be appreciated by those skilled in the art, such lead wires often inhibit patient movement, and/or may lead to sensor dislodgement or displacement by such movement. In addition, contact-type sensors pose a significant risk of injury to infants in particular, especially newborn or premature infants whose skin is very fragile and susceptible to damage (and thus not suitable for the use of adhesives, such as medical tape). For example, U.S. Pat. No. 7,008,371, the disclosure of which is hereby incorporated by reference into the present application, teaches a warming apparatus which includes a patient temperature probe 202 which is coupled to directly the patient. Another drawback of conventional warming devices which use contact-type sensors is that they are only useful for sensing those areas of the patient's body to which they are connected. As a result, other non-contacted areas of the patient may not receive the proper amount of warming therapy. A proposed solution to this challenge is the utilization of patient sensors which are not directly coupled to the patient's body, and/or which do not require adhesives, such as medical tape.

Accordingly, there is presently a need for a warming device that improves upon the energy and power inefficiencies of conventional devices, while eliminating the drawbacks associated with conventional contact-type sensors. It is also desirable to have a warming device that accurately senses all areas of a patient's body, and in response, selectively provides the appropriate amount of warming therapy to such areas.

SUMMARY OF THE INVENTION

An exemplary embodiment of the present invention comprises an apparatus including a patient support platform, a heater positioned relative to the patient support platform, the heater comprising a plurality of heating elements, and a controller coupled to the heater and a plurality of sensors for controlling the heat radiated from each of the plurality of heating elements.

An exemplary embodiment of the present invention also comprises a method of providing warming therapy to a patient disposed on a patient support platform, including, providing heating to the patient through a heater which includes a plurality of heating elements, sensing a temperature of the patient at each of a plurality of warming regions, and controlling the temperature of the patient by individually adjusting the heat radiated from one or more of the heating elements.

DETAILED DESCRIPTION

The present invention relates to warming device comprising a warming platform divided into a plurality of heating areas, and a radiant heating source including a plurality of heating segments, wherein each heating segment corresponds to a specific heating area of a warming platform. The warming device also includes a controller coupled to the radiant heating source for controlling the temperature in each warming region of the warming platform. Optionally, the warming device of the present invention may include a plurality of sensors positioned relative to the warming platform, and operatively coupled to the controller, for sensing a physiological parameter of a patient (e.g., body temperature), and for providing one or more sensor output signals to the controller to control the radiant heating source.

In operation, the warming device senses the temperature in each warming region of the warming platform, and generates one or more output signals indicative of such temperature(s).

These output signals are then processed and utilized to determine which warming regions, if any, require a temperature adjustment. If it is determined that one or more of the regions requires an adjustment, control signals are generated to selectively activate or deactivate the appropriate heating segments of the radiant heating source. Optionally, the output signals may be utilized to determined whether an "emergency" condition has occurred, or to determine the location of a patient on the warming platform. The output signals may also be utilized to generate thermal images of the patient receiving warming therapy (See FIG. 5), which may be displayed locally, via a video display unit, and/or remotely by way of a computer network interface via remote video display terminals.

Figure 2:
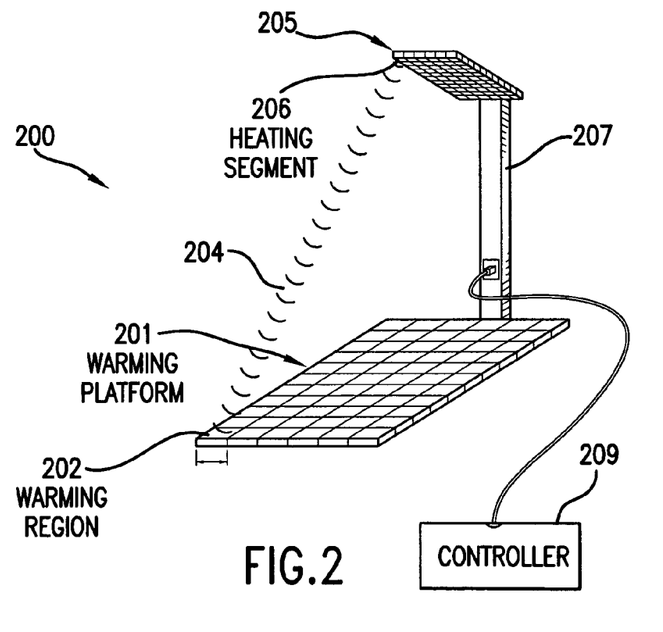
FIG. 2 is a perspective view of a warming device according to a first exemplary embodiment of the present invention.

FIG. 2 shows a warming device 200 according to a first exemplary embodiment of the present invention. The device 200 includes a warming platform 201, which is comprised of a plurality of warming regions 202, for supporting a patient receiving warming therapy, a radiant heating source 205, which is comprised of a plurality of heating segments 206, operatively positioned for monitoring the patient's body temperature and for emitting radiation 204 (e.g., heat) to the patient, as needed, and a controller 209 operatively coupled to the radiant heating source 205 for controlling the amount of radiation 204 emitted to the various warming regions 202 of the warming platform 201. In an exemplary embodiment, the warming platform 201 is comprised of one warming region 202 for each heating segment 206 of the heating source 205. However, there may be fewer warming regions 202 than heating segments, or vice versa, without departing from the scope of the present invention. The warming platform 201 may be constructed of any suitable material known to those of ordinary skill in the art. To limit the patient's movement, the warming platform 201 may comprise an optional mattress or support pad (not shown) constructed of a material such as slow recovery foam, or other suitable material.

For illustrative purposes, the radiant heating source 205 is shown mechanically connected to the warming platform 201 in FIG. 2 by way of a support bracket 207. However, it should be understood that any suitable means for positioning the radiant heating source 205 in a location suitable for emitting radiation 204 onto the warming platform 201 may be utilized without departing from the scope of the present invention. If a physical connection between the radiant heating source 205 and warming platform 201 is desired, any suitable connecting means known to those of ordinary skill in the art may be utilized.

In operation, the individual heating segments 206 of the radiant heating source 205 emit radiation 204 which is measured by sensors to determine the individual temperatures of the warming regions 202 of the warming platform 201. If the temperature at a specific warming region 202 is too cold, the controller 209 operates to increase the temperature at that region, by increasing the radiation 204 from the respective heating segment(s) 206. Similarly, if the temperature at a specific warming region 202 is too hot, the controller 209 operates to decrease the temperature at that region, by decreasing the radiation 204 from the respective heating segment(s) 206. This methodology also serves to heat only those portions of the warming platform 201 which contain a patient. For example, the portions of the warming platform where a portion of the patient's body is disposed will necessarily have a different temperature from those portions which include no portion of the patient's body. By sensing this temperature difference, the controller 209 can deactivate radiation in areas where no portion of the patient's body exists, thus reducing power consumption, and maintaining a cooler temperature in the area surrounding the warming device 200.

Additionally, the warming device 200 and method permits the heating of specific portions of the patient's body. For example, if a patient's hands and feet are colder than the rest of the patient's body, the sensors will detect this temperature variation and account for it by supplying added heat to the hands and feet of the patient (or more accurately, the area of the warming platform 201 above which the patient's hands and feet are disposed). Similarly, if the patient's extremities are colder than the rest of his or her body (or other than at a desired temperature), the sensors will detect the temperature variation and account for it by supplying less heat to the chest region of the patient. Thus, the warming device 200 permits an even distribution of heat across the patient's entire body. Alteration of the heating segments 206 to account for temperature variations within the patient's body may be accomplished automatically (e.g., the sensors continually work to maintain a constant and uniform body temperature of the patient), manually (e.g., a health care worker constantly or intermittently monitors the temperature of the patient, and actuates specific heating segments to equalize the difference), or a combination of manual and automatic procedures (e.g., a health care worker sets the patient's body temperature initially by actuating specific heating segments, and then the system works to automatically maintain the set heating levels). As discussed in more detail below, one or more monitors or sensors may be used to determine and/or display temperature variations across a patient's body (by viewing thermal images generated via a computer system and/or via thermal imaging devices), or to provide a thermal map of the patient, wherein different colors (or other known symbols) indicate different temperatures.

Figure 2A:
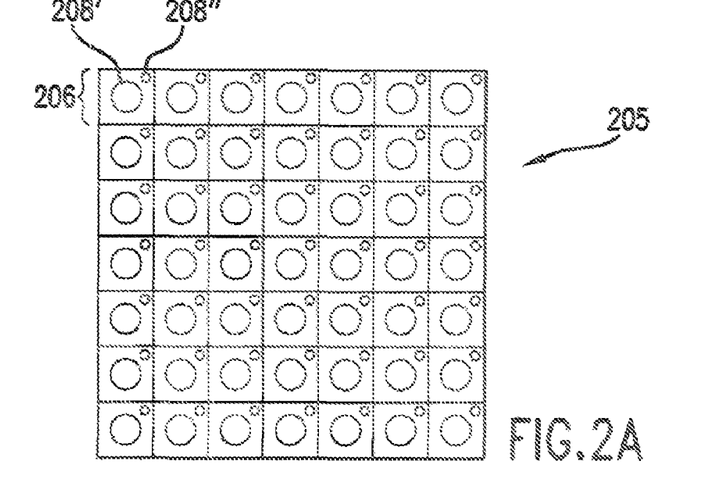
FIG. 2A is a bottom view of the radiant heating source shown in FIG. 2.

FIG. 2A shows a detail view of the exemplary radiant heating source 205. The radiant heating source 205 is comprised of a matrix of heating segments 206. Each heating segment 206 comprises one or more heating elements 208' for emitting radiation 204 towards a designated warming region 202 of the warming platform 201, and one or more sensors 208". The heating elements 208' comprise resistive heating members, but those of ordinary skill in the art will realize that many other different types of heating elements may be utilized without departing from the scope of the present invention. Although the heating elements 208' and sensors 208" are shown as being circular in FIG. 2A, those of ordinary skill in the art will realize that the elements and sensors may be of any suitable shape.

Each of the sensors 208" are configured to remotely sense a physiological parameter of the patient (e.g., skin temperature). These sensors 208" are arranged (and aimed) so that their respective field of sensitivity encompasses one or more corresponding warming regions 202 of the warming platform 201. As noted above, the number of sensors 208" in this exemplary embodiment directly corresponds to the number of warming regions 202, but other embodiments which include a number of sensors greater than (or less than) the number of warming regions are certainly within the scope of the present invention. Optionally, lenses and/or filters (not shown) may be incorporated into, or provided and positioned adjacent to, the sensors 208" to further focus the sensed parameter thereon.

In an alternate embodiment, one or more of the sensors 208" may comprise a thermal imaging device (e.g., thermal imaging camera) configured to sense, process, and generate thermal images of the sensed parameters. In such an embodiment, the thermal imaging device(s) may be positioned as sensor(s) relative to one or more warming region(s) 202 of the warming platform 201. Upon sensing temperature readings from the warming regions 202, the thermal imaging device(s) would independently process the temperature readings and generate corresponding thermal images. These thermal images may then be used to display temperature variations across a patient's body, wherein different colors (or other known symbols) indicate different temperatures. As will be appreciated by those skilled in the art, providing such thermal images will enable care providers to visually monitor patients' body temperatures, and to better understand changes in patients' warming requirements over time.

Referring again to FIG. 2A, the sensors 208" according to the first exemplary embodiment of the present invention may comprise infrared (IR) sensors, or any other suitable sensor known to those of ordinary skill in the art. Optionally, the sensors 208" may be configured to include any type of non-invasive laser (not shown), such as a low power laser diode, to assist in locating the patient on the warming platform 201, and determining temperature variations. In such an embodiment, a low power laser diode (or any other type of non-invasive laser) may be positioned adjacent to each sensor 208" and used to shine small laser beam(s) onto the patient. The location of a patient may be determined by monitoring (through a sensor or otherwise), the reflection of the laser beam(s) back from the warming platform 201. Then, based on the reflection(s), only those heating elements 208' corresponding to portions of the warming platform on which the patient is disposed would be activated. It is noted that the laser diode may run continuously, or may be activated intermittently to properly locate the patient.

The use of non-contacting sensors, such as sensors 208", eliminates the need for lead wires which are coupled directly to the patient, which as noted above, may inhibit patient movement and which may become dislodged and/or displaced by such movement. In addition, the risk of injury generally associated with conventional sensors is greatly reduced by using the heating elements 208' and sensors 208" as described above, particularly with regard to newborn or premature infants whose skin is very fragile and susceptible to damage (such as the kind caused by the conventional adhesives used to attach lead wires).

Referring again to FIG. 2, the warming device 200 includes a controller 209 configured to control a physiological parameter of the patient (e.g., body temperature), disposed on the warming platform 201. Although the controller 209 is depicted as being in wired remote communication with the warming device 200, it should be understood that the controller 209 may be sized and configured for integration into the warming platform 201, the bracket 207, the radiant heating source 205, or any other location known to those of ordinary skill in the art. The controller may also be configures to operate as a separate wireless unit which is coupled to the radiant heating source through radiofrequency (RF), or other means known to those of ordinary skill in the art.

Figure 3:
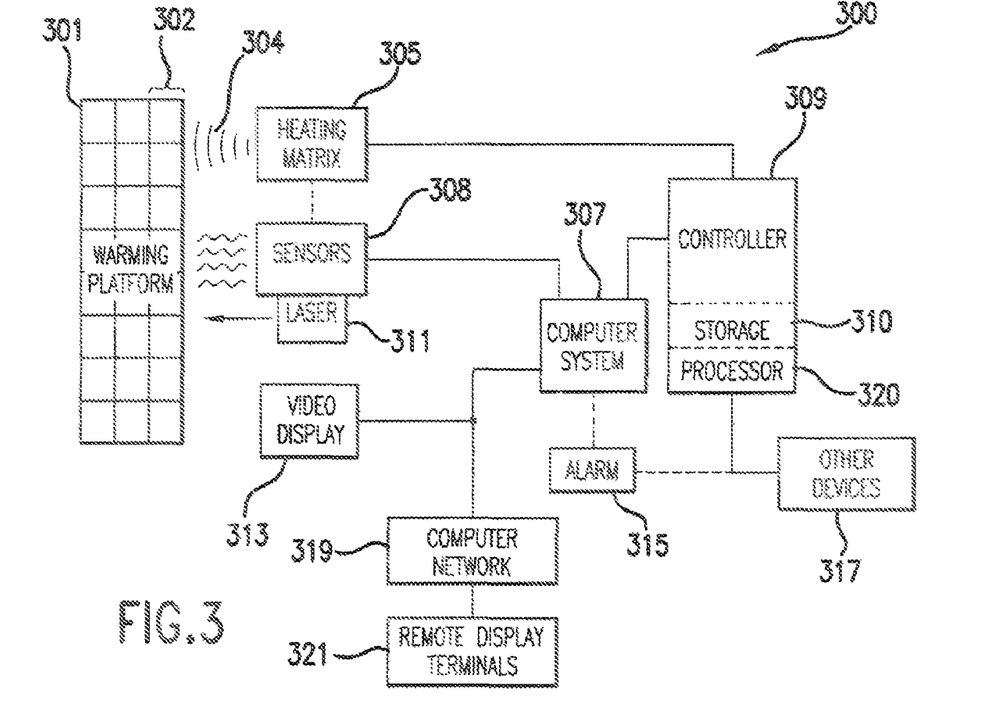
FIG. 3 is a block diagram showing a control system for the warming device shown in FIG. 2.

In an exemplary embodiment, the controller 209 includes at least a data storage means (e.g., computer memory, hard drive, etc.) for storing predetermined physiological parameter data (e.g., normal body temperature ranges, etc.), and a microprocessor for processing sensor signals, comparing the signals to the predetermined physiological data, and generating control signals for activating (or deactivating) the respective heating segments 206 (See FIG. 3). In one exemplary embodiment, the data storage means and microprocessor may be disposed within the controller 209, and in other exemplary embodiments they may be disposed in an external enclosure coupled to the controller 209 through a wired connection, or disposed in a remote location and accessed wirelessly through RF communications, or other known means.

In the exemplary embodiment, the controller 209 may be configured to continuously control the intensity and duration of the radiation 204 emitted from each of the heating elements 208' in response to that actual temperature sensed by the sensors 208". Alternatively, the controller 209 may be configured to discretely activate or deactivate the heating elements 208' if the sensed signals are below, or above, a predetermined temperature. In either case, the controller 209 receives and processes sensed signals generated by the sensors 208", and in response, generates and transmits control signals to the radiant heating source 205 for controlling the amount of radiation 204 emitted by each of the heating elements 208'. Optionally, the controller 209 may be utilized to control other devices in communication with the warming device 200 (shown as element 317 in FIG. 3). For example, the controller 209 may be operatively coupled to an alarm device (not shown) for signaling that a condition requiring immediate attention has occurred.

As noted above, in operation, a patient is positioned on the warming platform 201 in a position desirable for receiving warming therapy. The warming device 200 is then activated and the sensors 208" begin sensing the physiological parameter (e.g., body temperature), and generating control signals. For example, these control signals may comprise signals indicative of the temperature of each respective warming region 202 of the warming platform 201. In embodiments where one or more sensors 208" are configured as thermal imaging devices, the control signals may be processed by such thermal imaging devices and used to generate thermal images representative of the sensed parameters. Additionally or alternatively, the control signals generated by the sensors 208" may be coupled to the controller 209, where they are processed and utilized to control the temperature and/or environment of the patient within set parameters. Specifically, in response to the control signals the controller 209 activate and/or deactivates specific heating elements 208', or reduces the intensity of the heating elements 208', accordingly.

Besides controlling a patient's physiological parameters (e.g., body temperature), the control signals generated by the sensors 208" may also be utilized to locate the patient on the warming platform 201 prior to initiating heating. If, for example, the control signals indicate that the temperature in a particular warming region or regions 202 is higher than a threshold level (e.g., 30 Degrees Celsius (30° C.)), indicating the presence of a patient on the warming region(s), the controller 209 could determine that the patient is present in the warming region(s), and apply radiant heat to the region(s) through the activation of the corresponding heating elements 208'. Once the appropriate heating elements 208' have been activated, the sensors 208" will continue to monitor the specified physiological parameter (e.g., body temperature) in each respective warming regions 202, and the controller 209 will activate/deactivate the heating elements 208' to maintain a suitable warming environment for the patient.

Turning now to FIG. 3, a block diagram of an exemplary control system 300 for the warming device 200 is shown. The control system 300 includes a warming platform 301 for supporting a patient; a plurality of sensors 308 operatively positioned for monitoring the patient's position and/or physiological parameters (e.g., body temperature) and/or for independently generating thermal images representative of sensed physiological parameters; a matrix heating source 305 operatively positioned to emit radiation 304 onto warming regions 302 of the warming platform 301; and a controller 309 operatively coupled to the sensors 308 and to the matrix heating source 305 for controlling the amount of heat radiated to the various warming regions 302 in response to sensing signals provided by the sensors 308. Optionally, the system 300 may include a computer system 307 operatively coupled to the sensors 308 and/or to the controller 309 for use in processing sensor signals, generating thermal images according to processed sensor signals (See FIG. 5), and/or generating control signals. The computer system 307 may also be coupled, via an appropriate interface, to a computer network 319 and to remote display terminals 321, through which interested persons (e.g., health care providers, friends, relatives, etc.) can monitor the images and other relevant information accessible by the computer system 307. The system 300 may also include a local video display unit 313 operatively coupled to the computer system 307 to displaying the generated images to individuals disposed in the same (or adjacent) room as the warming platform 301. The system 300 may also comprise an alarm system 315 coupled to the computer system 307 and/or to the controller 309 for providing notice of certain emergency conditions. Additionally, the system 300 may comprise other devices 317 known to those of ordinary skill in the art in the field of warming therapy.

As discussed above, the exemplary warming platform 301 of the system 300 includes a plurality of warming regions 302, one for each heating element within the matrix heating source 305. As previously noted, greater or fewer warming regions 302 may be defined on the warming platform 301 to account for the particular configuration of the matrix heating source 305. The sensors 308 may be disposed within the same enclosure as the heating source (as shown in FIG. 2A), or may be disposed within a separate enclosure. For example, in an embodiment where one or more sensors 308 are configured as thermal imaging devices, such sensor(s) 308 may be disposed in a separate enclosure adjacent to the warming platform 301. In an alternative embodiment, where the sensors 308 not configured as thermal imaging devices, but are simply configured to sense physiological parameters of a patient, the sensors 308 may be disposed within, or adjacent to, the warming platform 301. If the sensors are mounted within the warming platform 301, they may be aimed directly at a corresponding heating element of the matrix heating source 305. In this manner, a failure to sense the direct heat of a respective heating element (due to the body of the patient blocking the sensing path) may be used to determine the location of the patient on the warming platform 301. Alternatively, sensed position signals from platform-mounted position sensors (e.g., lasers) may similarly be used to detect the presence/location of the patient on the warming platform 301. For example, the location of a patient may be determined by monitoring (through a sensor or otherwise), the reflection of the laser beam back from the warming platform 301.

As noted above, the system 300 may additionally include one or more laser beams generated by a laser source 311 for shining small non-invasive laser beam(s) onto the warming platform 301, in order to locate the patient on the warming platform 301. The laser source may be used in place of, or in addition to, using the sensors 308 to locate the patient. The laser source 311 may include a sensor therein which detects the reflection of the laser beam back from the warming platform 301, and a processor which determines the location of the patient from the reflected laser beams.

In an exemplary embodiment, the controller 309 includes at least a data storage means 310 (e.g., computer memory, hard drive, etc.) for storing predetermined physiological parameter data (e.g., normal body temperature ranges, etc.), and a microprocessor 320 for processing sensor signals, comparing the signals to the predetermined physiological data, and generating control signals for activating (or deactivating) the respective heating elements of the matrix heating source 305. In the exemplary embodiment shown in FIG. 3, the data storage means 310 and microprocessor 320 are disposed within the controller 309 enclosure, however, they may alternatively be disposed in an external enclosure coupled to the controller 309 through a wired connection, or disposed in a remote location and accessed wirelessly through RF communications, or other known means.

In one embodiment, the controller 309 may be configured to control the intensity (and duration) of thermal radiation of each heating segments comprising the matrix heating source 305 in response to the actual temperature sensed by the sensors 308. Alternatively, the controller 309 may be configured to activate and deactivate the heating segments according to whether sensed signals are below or above a predetermined threshold temperature. In either case, the controller 309 receives and processes sensed signals generated by the sensors 308, and in response, generates and transmits control signals to control the amount of heat radiated 304 by each of the heating segments onto the warming platform 301.

Figure 5:
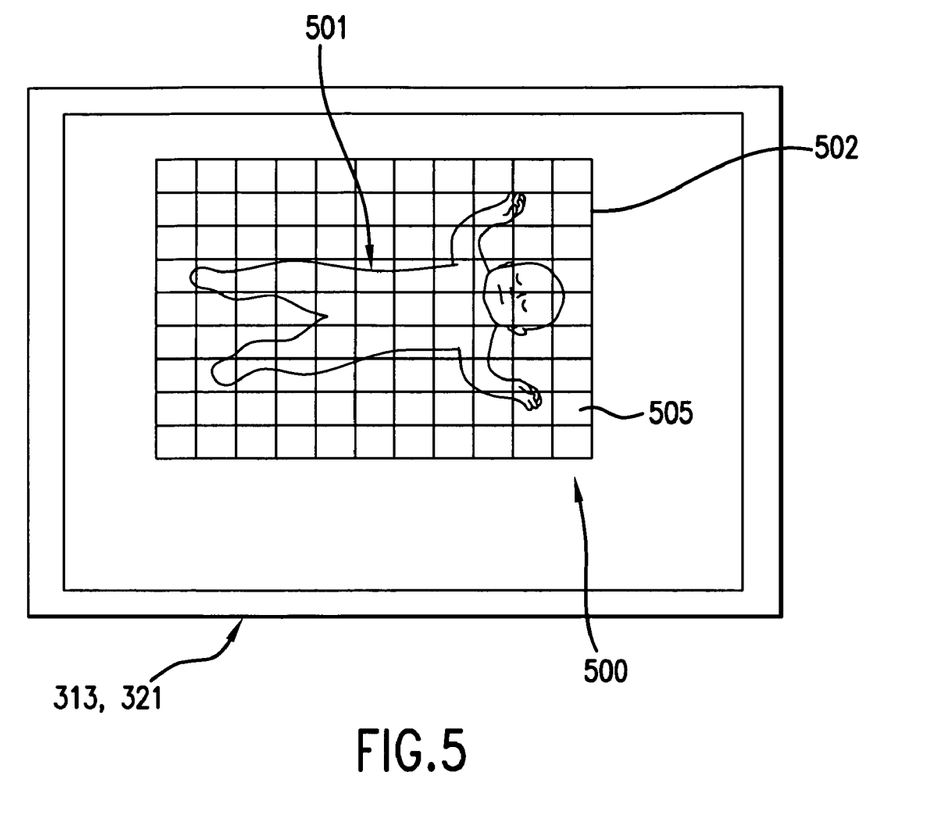
FIG. 5 shows a display monitor of the warming device according to the first exemplary embodiment of the present invention, which is displaying an exemplary thermal image of a patient.

The computer system 307 shown in FIG. 3 may be utilized to generate representative thermal images of the patient's body temperature (See FIG. 5). Alternatively, thermal images may be generated independently by thermal imaging devices and them provided to the computer system 307 for storage, further processing, and/or display. The thermal images, together with other data and information stored on the computer system 307, may then be displayed locally via a video display unit 313, and/or remotely to one or more remote display terminals 321 over a computer network 319. Although the video display unit 313 is shown as being an independent unit, it should be noted that the video display unit may be sized and configured for integration into either (or both) of the warming platform 301 or the matrix heating source 305.

In operation, a patient is positioned on the heating platform 301 in a position desirable for receiving warming therapy. The sensors 308, positioned relative to the warming platform 301, are then activated and begin sensing a physiological parameter of the patient (e.g., body temperature), and generating control signals. For example, these control signals may comprise signals indicative of the temperature of each respective warming region 302 of the warming platform 301. The control signals generated by the sensors 308 are coupled to the controller 309, where they are processed and utilized to control the temperature of the patient within set parameters. Specifically, in response to the control signals the controller 309 activates and/or deactivates specific heating elements of the matrix heating source 305, or reduces the intensity of the heating elements, accordingly.

In processing the control signals, the controller 309 compares the control signals to predetermined thresholds (optionally stored in the data storage means 310), and in turn, determines whether to activate or deactivate certain heating elements of the matrix heating source, or change their intensity. For example, if body temperature is the physiological parameter, temperature signals generated by the sensors 308 which are below a baseline threshold temperature indicate that the patient's body temperature (in a particular warming region 302) is below a desired temperature, and as a result, heating element(s) corresponding to the specific warming region(s) 302 ought to be activated (or intensified). Similarly, temperature signals indicative of temperatures at or above a ceiling threshold indicate that the patient's body temperature (in a particular warming region 302) has reached the desired temperature and accordingly, heating element(s) corresponding to certain warming region(s) 302 may be disabled (or decreased in intensity).

If, at any time during the initial activation of the heating elements of the matrix heating source 305, or at any time during the monitoring of the patient, it is determined that a condition requiring immediate attention has occurred (e.g., a body temperature reading in excess of 102 Degrees Fahrenheit (102° F.)/39 Degrees Celsius (39° C.) has been sensed), the controller 309 may generate control signals to trigger an alarm 315. Conditions necessitating the triggering of the alarm 315 may include, for example, a sudden drop or spike in the patient's temperature, and/or a change in the relative position of the patient on the heating platform 301. To this end, acceptable patient temperature ranges may be stored in the data storage means 310. The alarm 315 may include an audible alarm, such as a buzzer or siren, or a visual alarm, such as illumination of an indicator light, or any other signal or combination thereof known to those of ordinary skill in the art and indicative of a condition needing immediate attention.

As discussed above, the position of the patient on the heating platform 301 may also be determined using optional lasers (e.g., low power laser diodes) in addition to, or as a substitute for the sensors 308. When only the sensors 308 are used to determine location, an additional threshold temperature may be stored in the data storage means 310, such threshold temperature indicating the presence or absence of a patient on the heating platform 301. For example, a threshold level of 30 Degrees Celsius (30° C.) is appropriate for determining the presence of a patient (or portion thereof) on the warming region(s) 302 of heating platform 301. This is because if the patient (or portion thereof) is present, the temperature reading will be much higher than 30° C., if the patient is not present, it will be much lower than 30° C.

In addition to being utilized to determine a patient's temperature and/or position, the control signals generated by the sensors 308 may also be utilized to generate thermal images indicative of the temperature(s) of the entirety of the patient (See FIG. 5). These thermal images may be, in turn, utilized to generate one or more control signals for adjusting the heat radiated from one or more of the heating elements of matrix heating source 305. The thermal images may be independently generated by the sensors 308 (e.g., those configured as thermal imaging devices), or via the computer system 307. If generated via the computer system 307, the sensors 308, being operatively coupled to the computer system 307, generate and provide sensed Control/temperature signals to the computer system 307. The computer system 307 then processes and utilizes the control/temperature signals to generate thermal images. To that end, the computer system 307 may include temperature processing and/or imaging software loaded thereon which analyzes the control signals generated by the sensors, and converts them to representative thermal images. The thermal images may then be displayed for viewing by an on-site care provider via the local video display unit 313, and/or by off-site viewers via remote display terminals 321. As noted above, the thermal images may utilized to monitor the temperature variations in a patient's body, so that the system 300 can account for them by activating or deactivating specific heating elements of the matrix heating source 305, or by raising or lowering the heat applied to such elements.

Figure 4:
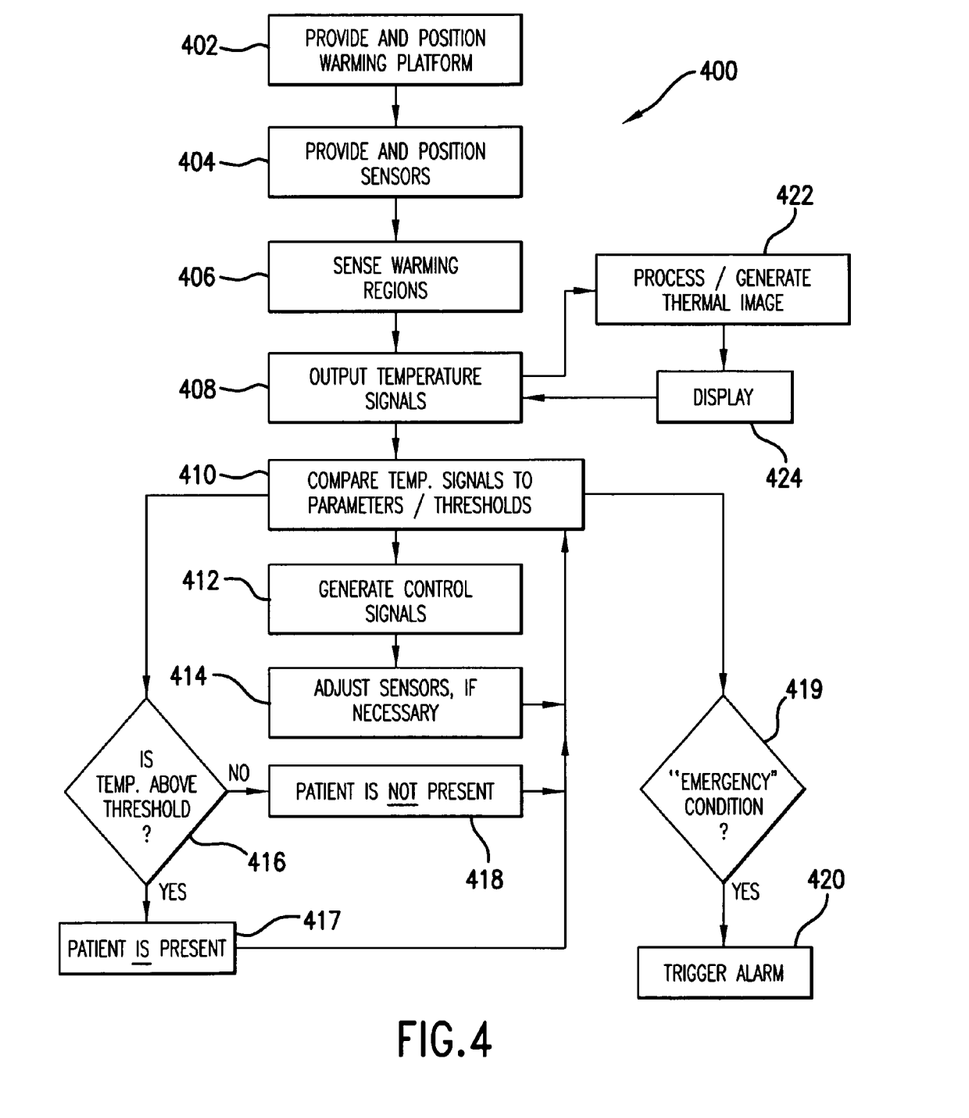
FIG. 4 is a flow chart showing the method for sensing and adjusting the temperature of the warming device shown in FIG. 2.

Referring now to FIG. 4, a method 400 for providing warming therapy to a patient according to a first exemplary embodiment of the present invention is illustrated. The method 400 begins with the provision of a patient on a warming platform (e.g., warming platform 301; FIG. 3) which is situated to receive radiant heat from a heating source (e.g., matrix heating source 305; FIG. 3) (step 402). As discussed above, each respective element of the heating source may comprise one or more heating elements. Further, each respective element of the heating source may be positioned to warm a designated warming region (e.g., warming region 302; FIG. 3) on the warming platform. Next, a plurality of non-contact sensors is provided and positioned relative to the warming platform, such that each sensor's field of sensitivity encompasses one or more corresponding warming regions (step 404). As discussed above, the non-contact sensors may be formed as part of the heating source, the warming platform, or as a separate unit. Once the heating source and sensors are properly positioned, the sensors are activated to begin sensing the temperature in the respective warming regions (step 406). Sensed temperature(s) from the sensors are then output as temperature signals (step 408) for further processing by a controller.

The temperature signals generated by the sensors are then compared to predefined temperature parameters to determine which (if any) warming regions require a temperature adjustment (step 410). Control signals that are consistent with the determinations of step 410 are then generated (step 412) and used activate, deactivate, and/or adjust one or more heating elements of the heating source, if necessary, until the patient exudes the desired warming temperature (step 414). Once optimal temperature is achieved, the sensors continue to monitor the patient's temperature and make further adjustments as necessary. Selectively activating, deactivating, and/or adjusting the heating segments in this manner will enable the patient to consistently experience a desirable warming environment, while at the same time minimizing unnecessary heat loss and maximizing system efficiency.

The temperature signals generated at step 408 may optionally be utilized to determine the location of a patient on the warming platform. For example, the control signals may be compared to predetermined temperature thresholds to determine where the patient is disposed on the warming platform (step 416). If the control signal corresponding to a particular warming region of the warming platform indicates a temperature above a certain threshold (e.g., 30° C.), the patient is determined to be present in the region (step 417). Conversely, if the control signal corresponding to a particular warming region of the warming platform indicates a temperature below a certain threshold, the patient is determined to be absent from the region (step 418). The process is repeated for each warming region until the relative position of the patient can be accurately determined. For example, to save processing time, the process may start with warming regions disposed about the outer edge of the warming platform and work inward, as the patient is typically placed in the center of the warming platform to start.

The temperature signals generated at step 408 may also optionally be utilized to determine an alarm condition. As noted above, examples of alarm conditions may include, for example, a sudden drop (or spike) in the patient's temperature, a dangerous position of a patient on the warming platform, and the like. For example, where the alarm condition is the patient's temperature, the temperature signals generated in step 406 may be compared to predetermined temperature thresholds to determine whether the patient's temperature has exceeded (or dropped below) an acceptable level (step 419). If the temperature signal indicates a significant change (up or down) an alarm is triggered (step 420). Where the alarm condition is position, the patient's position must first be determined using the process described with reference to steps 416-418 above. Once an initial position is determined and stored, the position over time is compared to the initial position, to determine if there are any radical movements or changes (step 419). If there are, the alarm is triggered (step 420).

The temperature signals generated at step 408 may also be utilized to generate thermal images of the patient indicative of the temperature of the patient in each of the warming regions (step 422). Once generated, the thermal images may be displayed locally to on-site viewers (via a video display unit, for example), or remotely by way of a computer network to off-site viewers (step 424). In either case, the images may be generated by, for example, a computer system running a temperature processing software capable of converting temperature signals into thermal images. Alternatively, the thermal images may be generated via one or more thermal imaging devices (e.g., thermal imaging camera) configured to sense and independently process temperature readings. In such an embodiment, one or more thermal imaging device(s) would be positioned as sensor(s) relative to the warming regions (step 404). Then, upon sensing temperature readings from the warming regions (step 406), the thermal imaging device(s) would independently process the temperature readings and generate corresponding thermal images (step 422) for display (step 424).

FIG. 5 shows an exemplary display monitor (e.g., monitors 313, 321) of the above-described system 300 displaying an exemplary thermal image 500 of a patient. The thermal image 500 may include a patient image 501, and a grid image 502. The patient image 501 is comprised of different colors (not shown), indicating various temperature levels, as well known to those of ordinary skill in the art. For example, the color blue may indicate temperatures below 75° F., the color yellow may indicate temperatures between 75-95° F., the color green may indicate temperatures between 96-101° F. (including the normal body temperature of an adult of 98.6° F.), and the color red may indicate temperatures of 102° F. and above. Obviously, these ranges are only exemplary, and may be made smaller (e.g., ranges of 2-3° F. for each color) to more accurately determine the exact temperature of each portion of a patient's body. As noted above, the thermal image may also include a grid image 502, which may represent the warming platform (201, 301) and the different warming regions (202, 302) thereof. To this end, the grid image 502 may be subdivided into a plurality of cells 505, where each cell corresponds to a warming region (202, 302). The grid image 502 may additionally include alphanumeric symbols which allow the specification of each cell 505 of the grid image. For example, the grid image 502 may include the letters A-F horizontally, and the numbers 1-6 vertically, such that the designator "B3" specifies a particular cell (505) of the grid image 502. In this manner, a health care worker can examine the thermal image 500 and immediately determine which cells require more or less warming. Similarly, the health care worker can specify to the system 300 that more or less heat should be provided to particular cells 505, and the system will react by engaging the corresponding heating elements of the matrix heating source 305. Alternatively, this process may be performed automatically, or semi-automatically, by the system 300.

Although exemplary embodiments of the present invention have been described above for use in procedures involving infants, those of ordinary skill in the art will realize that the warming device 200, system 300 and method 400 of the present invention may be used for other types of operations and procedures, including for children and adults.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus comprising:
   a patient support platform;
   a radiant heater positioned relative to the patient support platform and at a position overtop of the patient support platform, said radiant heater comprising a plurality of heating elements; and,
   a controller coupled to the heater and a plurality of sensors for controlling the heat radiated from each of the plurality of heating elements,
   wherein the patient support platform is comprised of a plurality of warming regions and wherein each of the plurality of warming regions corresponds directly to a respective one of the plurality of heating elements.

2. The apparatus of claim 1, wherein the plurality of sensors operate to sense a physiological parameter of a patient disposed on the patient support platform.

3. The apparatus of claim 1, wherein the controller comprises:
   data storage means for storing at least physiological parameter data; and
   a microprocessor coupled to the data storage means, for comparing at least one first output signal from the plurality of sensors to the physiological parameter data, and for generating at least one first control signal responsive to the comparison for selectively activating or deactivating one or more of the heating elements.

4. The apparatus of claim 3, further comprising an alarm coupled to the microprocessor for generating at least one of an audio or visual alarm.

5. The apparatus of claim 3, wherein the plurality of sensors comprise a plurality of infrared sensors.

6. The apparatus of claim 1, wherein each of the plurality of heating elements are located adjacent to each of the plurality of sensors.

7. The apparatus of claim 1, wherein the plurality of sensors are disposed within the patient support platform.

8. The apparatus of claim 1, wherein the plurality of sensors are disposed within the heater.

9. The apparatus of claim 1, further comprising at least one video display unit coupled to the controller.

10. The apparatus of claim 1, further comprising at least one laser source, said laser source capable of determining the relative position of a patient on the patient support platform.

11. The apparatus of claim 2, wherein the physiological parameter comprises body temperature.

12. The apparatus of claim 11, wherein the apparatus operates to maintain a substantially uniform temperature across a patient's entire body.

13. A method of providing warming therapy to a patient disposed on a patient support platform, the method comprising:
    providing heating to the patient through a radiant heater which includes a plurality of heating elements, said radiant heater disposed at a position overtop of the patient;
    sensing a temperature of the patient at each of a plurality of warming regions; and
    controlling the temperature of the patient by individually adjusting the heat radiated from one or more of the heating elements,
    wherein each heating element corresponds directly to a respective one of the plurality of warming regions.

14. The method of claim 13, wherein the step of sensing a temperature of the patient further comprises:
generating one or more temperature signals, each temperature signal corresponding to a separate warming region.

15. The method of claim 13, wherein the step of controlling the temperature of the patient comprises:
storing temperature data in a data storage means;
comparing the one or more temperature signals to the stored temperature data; and
generating one or more control signals for selectively activating or deactivating one or more of the plurality of heating elements.

16. The method of claim 15, comprising the further step of generating at least one of an audio and visual alarm signal if one or more of the temperature signals exceeds, or falls below, a predetermined temperature threshold.

17. The method of claim 15, comprising the further steps of:
processing the temperature signals to generate one or more thermal images of the patient; and
displaying, on a video display unit, one or more of the thermal images.

18. The method of claim 17, comprising the further steps of:
utilizing the one or more thermal images of the patient to generate one or more control signals for adjusting the heat radiated from one or more of the heating elements.

19. The method of claim 13, comprising the further step of:
generating one or more temperature signals, each temperature signal corresponding to a separate warming region;
comparing the one or more temperature signals to predetermined temperature threshold; and
determining that the patient is occupying the warming region if the temperature signal indicates a temperature greater than the predetermined temperature threshold; and,
determining that the patient is not occupying the warming region if the temperature signal indicates a temperature less than the predetermined temperature threshold.

20. The method of claim 19, wherein the step of generating one or more temperature signals comprises:
generating one or more temperature signals corresponding to warming regions which are disposed closest to the periphery of the patient support platform; and,
generating one or more temperature signals corresponding to warming regions which are disposed closest to the middle of the patient support platform.

* * * * *